(12) United States Patent
Ziegler et al.

(10) Patent No.: US 7,109,158 B2
(45) Date of Patent: Sep. 19, 2006

(54) AROMATIC COMPOSITION CONSISTING OF HLA MOLECULES

(75) Inventors: Andreas Ziegler, Berlin (DE); Barbara Uchanska-Ziegler, Berlin (DE); Karin Golz-Berner, Monaco (MC); Leonhard Zastrow, Monaco (MC)

(73) Assignee: Coty B.V., Haarlem (NL)

( * ) Notice: Subject to any disclaimer, the term of this patent is extended or adjusted under 35 U.S.C. 154(b) by 562 days.

(21) Appl. No.: 10/258,364

(22) PCT Filed: Apr. 26, 2001

(86) PCT No.: PCT/DE01/01609

§ 371 (c)(1),
(2), (4) Date: Oct. 22, 2002

(87) PCT Pub. No.: WO01/81374

PCT Pub. Date: Nov. 1, 2001

(65) Prior Publication Data

US 2003/0087796 A1 May 8, 2003

(30) Foreign Application Priority Data

Apr. 27, 2000 (DE) ................................. 100 21 579

(51) Int. Cl.
*A61K 7/46* (2006.01)
(52) U.S. Cl. ........................................................ 512/1
(58) Field of Classification Search ...................... 512/1
See application file for complete search history.

(56) References Cited

OTHER PUBLICATIONS

Jacob et al. "Paternally inherited HLA alleles are assiociated with women's choice of male odor." Nature Genetics, v. 30, Feb. 2002 (www.mindfullyorg/Health/Women-Choice-Male-OdorFeb02.htm).*

Milinski et al. "Evidence for MHC-correlated perfume preferences in humans." Behavoiral Ecology, vol. 12 No. 2: 140-149, 2001 (http://beheco.oupjournals.org/cgi/content/abstract/12/2/140).*
McDonald, Adamashvili; Soluble HLA: a review of the Literature; 1998; 129:258986.
Sommerville et al.; Volatile Indentity Signals in Human Axillary Sweat: the Possible Influence of MHC Class I Genes; 1996; 124:114831.
Zavazava et al.; Regulation of Soluble MHC Class I Molecules; 1996; 124:114826.
Zavazava et al.; Soluble MHC Class I Molecules in Human Body Fluids; 1995; 122:53522.
Eggert, Ferstl and Muller-Ruchholtz; MHC and Olfactory Communication in Humans; 2000; 133:71714.
Wobst et al.; Molecular Forms of Soluble HLA in Body Fluids: Potential Determinants of Body Odor Cues; 1999; 131:241667.

* cited by examiner

*Primary Examiner*—Monique T. Cole
(74) *Attorney, Agent, or Firm*—Akerman Senterfitt; Stephan A. Pendorf

(57) ABSTRACT

The invention relates to novel aromatic compositions consisting of HLA molecules, which two different potential perfume carriers are assigned. The invention aims at developing novel aromatic compositions consisting of HLA molecules based on the selection of alleles of genes which are relevant from an olfactory viewpoint and subsequent processing thereof. According to the invention, the aromatic compositions are produced by selecting one allele amongst known class I HLA alleles, which differs in at least one characteristic from other alleles of HLA class I molecules and which is present in less than 5% of individuals of the world population; the protein that is coded for by the selected allele undergoes assembly in the presence of $\beta_2$-microglobulin ($\beta_2$m); the formed HLA class I molecules are purified with the bonded peptides and fragmented with the protease, and the odor-active substances resulting from fragmentation are added as individual components or as a mixture to a cosmetic preparation.

9 Claims, 2 Drawing Sheets

AROMATIC COMPOSITION CONSISTING OF HLA MOLECULES

BACKGROUND OF THE INVENTION

1. Field of the Invention

The present invention relates to new perfume compositions, each assigned to two different potential scent carriers (partners).

2. Description of the Related Art

A plurality of scents of different provenience are known from the state of the art; these scents have been and will be used to have a positive influence on the presumably inadequate natural body odor by means of more or less pleasant smelling essential oils, perfumes or soaps. In recent years, it has become known that genetic factors may be responsible for an individual's natural body odor and thus also for his or her attractiveness to other partners. Specific studies on volunteers (*Am. J. Hum. Genet.* 61, 505–51 (1997)) have shown that the choice of partners might be influenced by odors by way of polymorphic genes of the major histocompatibility complex ((MHC=major histocompatibility complex; HLA=human leukocyte antigen)). HLA genes are in a range of approximately 4 million base pairs (bp) on human chromosome 6. So far attempts to make an unambiguous olfactory assignment of molecules to the development of a specific individual odor have not been successful. However, there are signs that MHC molecules play a causal role in the creation of a specific individual odor profile (*Proc. Natl. Acad. Sci. USA* 94, 2210–2214, 1997; *Proc. Natl. Acad. Sci. USA* 96, 1522–1525, 1999).

SUMMARY OF THE INVENTION

The object of this invention is to develop a perfume composition which makes it possible to produce odor-specific substances on the basis of a selection of certain alleles of olfactorily relevant genes and subsequent treatment of their synthesis products; in the form of two separate formulations, these substances should then impart a different but mutual attractiveness to different partners.

According to this invention, a perfume composition is made available which is produced by a method in which a) of known HLA alleles of class I, an allele which differs by at least one feature from other alleles of the HLA class I molecules is selected, and which occurs in less. than 5% of the world's population; or b) HLA alleles of class I produce by mutation of HLA alleles of class I already present and which do not occur naturally and thus have an incidence of 0% are selected; and c) the protein for which the selected allele codes is subjected to an assembling operation in the presence of $\beta_2$-microglobulin ($\beta_2$m), including single-chain constructs of HLA heavy chains of class I and $\beta_2$m by forming a plurality of different peptides with a length of typically 7 to 12 amino acids and with free N- and C-termini to form soluble HLA class I molecules consisting of the extracellular domains $\alpha_1$, $\alpha_2$ and $\alpha_3$, $\beta_2$m and a peptide, whereby the peptide is present in bound form in a peptide binding pocket of the HLA molecule formed by the extracellular domains $\alpha_1$, and $\alpha_2$; and d) the HLA class I molecule thus formed with the bound peptide is separated from the other constituents in a purification step; and e) the purified HLA class I molecule is subjected to fragmentation with one or more proteases; and f) the substances that are active in forming the odor and are formed in fragmentation are added as individual components or as a mixture to the cosmetic preparation, optionally after first separating the other substances.

To facilitate an understanding of this invention, the explanation of intracorporeal formation of HLA class I molecules is given below.

It is known that mammals have the ability to differentiate between their own tissue and that of another species as well as that of other individuals of their species. With the help of transplantation studies in the mouse, different genes which are responsible for rapid rejection of foreign tissue have been identified in the H-2 region on chromosome 17. This gene complex has since then become known as the major histocompatibility complex (MHC). Human MHC is located on the short arm of chromosome 6 and is known as HLA (human leukocyte antigen) complex. It contains, among other things, the genes for the MHC class I proteins HLA-A, HLA-B and HLA-C, as well as HLA class II proteins. HLA molecules bind intracellular peptides which are formed in degradation of cytosolic (typically MHC class I) or extracellular proteins (typically MHC class II) and transport them to the cell surface where HLA/peptide complexes can be recognized by the T-lymphocytes of the immune system. Other gene products coded in MHC are involved in the formation of peptide fragments and their transport.

HLA class I molecules consists of a membrane-anchoring heavy chain (43 kDa) and a noncovalently associated light chain, $\beta_2$-microglobulin ($\beta_2$m; 12 kDa; see FIG. 1). The heavy chain is composed of three extracellular domains ($\alpha_1$, $\alpha_2$, $\alpha_3$) each with approximately 90 amino acids, a transmembranal region approximately 25 amino acids long and a C-terminal cytoplasmic region. The asparagine preserved in position 86 of the $\alpha_1$ domains has undergone N-glycosylation in all HLA class I proteins. $\beta_2$-Microglobulin is not bound to membrane and has only one domain.

The three-dimensional structure of HLA class I molecules shown in FIG. 1 is known from x-ray crystallographic studies (see, for example, *J. Mol. Biol.*, Vol. 285, 645–653, 1999). $\beta_2$-Microglobulin and the membrane-proximal domains of the heavy chain ($\alpha_3$) having the characteristic folding of molecules of the immunoglobulin superfamily support and stabilize the peptide bonding array formed by the $\alpha_1$ and $\alpha_2$ domains in common, where the peptide is enclosed between two $\alpha$Zhelices, which are situated on a surface formed by one of eight antiparallel $\beta$Zstrands (FIG. 3).

The heavy HLA chain is subject to a high polymorphism, but $\beta_2$m is identical in all HLA class I molecules and is also coded on chromosome 15 outside the HLA complex. So far approximately 70 HLA-A alleles, approximately 200 HLA-B alleles and approximately 70 HLA-C alleles are known, each individual allele of which can express a maximum of two alleles per gene locus. The variability of the alleles is limited almost completely to the $\alpha_1$ and $\alpha_2$ domains and concerns mainly amino acids whose side chains point into the peptide bonding array or to the T-cell receptor.

The bottom of the peptide bonding array consists of six differently manifested indentations or pockets which are formed by the amino acid side chains of the HLA protein. The peptides presented here usually have a length of eight or nine amino acids and are bound in an elongated conformation (see FIG. 3). A preserved network of hydrogen ridges positions the free N- and C-termini in the pockets at the ends of the bonding array and thus determines the orientation of the peptides. Additional allele-specific contacts exist between the side chains of the peptide and the polymorphic amino acids of the HLA protein. The pockets formed by the latter are capable of completely accommodating individual amino acid residues of the peptide which point downward into the bonding array. These side chains are also referred to as "anchor residues" because they anchor the peptide securely in the bonding array. Each HLA protein has at least one deep pocket formed by polymorphic amino acids, the pocket being specific for the respective allele. Only peptides having suitable anchor residues can be bound.

Both chains of an HLA class I molecule are synthesized separately in the cell and are conveyed cotranslationally into the endoplasmic reticulum (ER) where assembly of the heavy chain (HC, heavy chain) with $\beta_2$-microglobulin ($\beta_2$m) and a peptide, to form functional complexes takes place. A number of different proteins are involved in this coordinated folding process (*Immunol. Today* 21 (2000), 83–88).

This intracellular process can be completed in vitro in a similar manner by causing the three components of the trimolecular end product, i.e., an HLA class I molecule, to interact with one another in a suitable medium. In this connection, it is possible to bring the DNA molecules that code for these three components to a expression in one, two or three constructs so that the three components may be present either individually or as a dimeric or trimeric protein for further processing. Of the known alleles, a selection is made such that preference is given to the rarest possible allele (i.e., occurring in less than 5% of the world's population) over an allele occurring more commonly in the population. The alleles HLA-A*6601 and HLA-B*7301 may be used as an example because they occur extremely rarely (in less than 1% of the population of Central Europe). It should be noted here that sequence differences between HLA class I alleles usually involve more than just a single nucleotide position, so that the corresponding protein products may differ in a variable number of amino acids. These differences characteristically lead to differences in peptide binding behavior. The two HLA molecules HLA-B35 and HLA-B53 may be used as an example because they differ only in the presence of the Bw6-(B35) and Bw4-(B53) determinants, i.e., in five altered amino acids. As a rule, the bound peptides contain a tyrosine (B35) as the C-terminal anchor, where several amino acids are tolerated as the C-terminus of the peptide of HLA-B53 molecules. The other anchor in peptide position 2, however, is a proline in both molecules due to the identity of the molecules in the region of the B pocket which binds this proline.

The relevant information for selecting alleles and peptides is accessible to those skilled in the art and also to the general public (e.g., on the Internet at http://www.ebi.ac.uk/imgt/hla/ for DNA sequences and protein sequences of HLA molecules; ftp://ftp.wehi.deu.au/pub/biology/mhcpep/ or http//134.2.96.221/scripts/hlaserver.dll/home.htm for peptide sequences). Those skilled in the art can also deduce from this which alleles have which features and at what frequency they occur.

Another embodiment of this invention consists of constructing artificial HLA class I alleles and synthesizing the respective proteins which do not occur in the human population according to the information currently available and which optionally have an altered peptide binding behavior. For example, it is possible through in vitro mutagenesis to replace the B pocket of the HLA-B27 molecule, which preferentially binds an arginine in peptide position 2, with the B pocket of the HLA-A2 molecule, which leads to binding of peptides having a hydrophobic amino acid such as leucine in the peptide position 2. The term "allele" therefore includes both natural and artificial alleles.

After the selection, the soluble extracellular portion of the protein(s), i.e., the $\alpha_1$, $\alpha_2$ and $\alpha_3$ domains, are synthesized according to this invention and then in vitro assembly takes place in such a manner that in the presence of $\beta_2$m in a reconstitution solution at a temperature in the range of 0 to 40° C., the protein of the selected HLA allele is introduced into a peptide pool with different peptides of 7 to 12 amino acids, preferably 8 to 9 amino acids, and incubated for a period of 1 to 7 days. The peptide pool contains in particular peptides having suitable "anchors" (anchor amino acids, see above) such as proline in position 2 and tyrosine in position 8 or 9 of a peptide in the case of the HLA-B35 molecule. The octamer VPLRPMTY or the nonamer LPPLDITPY (*J. Mol. Biol.* 285, 645–653, 1999) may be used as such a peptide, for example.

The reconstituted trimeric HLA class I molecule is then separated by chromatography, e.g., by high-performance liquid chromatography (HPLC) or by FPLC from the other constituents of the mixture such as unbound peptides, $\beta_2$m, etc. Correct folding of the reconstituted molecule and thus the native conformation are proven, e.g., with the help of conformation-dependent antibodies in the ELISA test and by means of immunoprecipitation (*Eur. J. Immunol.*, Vol. 23, 734–738, 1993; *Hum. Immunol.* 61, 408–418, 2000).

In a special embodiment of this invention, the HLA class I molecule formed according to point c) or d) is placed in a mammalian serum, preferably a mouse serum, in particular a serum from $\beta_2$m(−/−) mice for a period of 1 to 36 hours, preferably 18 to 36 hours at 4° C. to 40° C., preferably 37° C., before the subsequent fragmentation. Therefore, additional substances are optionally bound to the HLA molecule.

In subsequent fragmentation of the purified HLA class I molecule, a plurality of proteases may be used.

The proteases are preferably selected from proteases such as serine proteases, cysteine proteases, aspartate proteases and metal proteases as well as peptidases such as amino peptidases, dipeptidases, dipeptidylcarboxypeptidases, carboxypeptidases, omega-peptidases. For example, pronase from *Streptomyces griseus* (Sigma Pronase type XIV) is preferred (*Proc. Natl. Acad. Sci. USA*, Vol. 96, 1522–1525, 1999).

Fragmentation with pronase may take place, for example, at room temperature for two hours, whereby the concentration may vary as a function of the experimental conditions.

For reconstitution of soluble HLA-A or HLA-B peptide complexes, a reconstitution buffer may optionally be added, e.g., 400 mM L-Arg-HCl, 2 mM EDTA, 5 mM reduced glutathione, 0.55 mM oxidized glutathione, 100 mM Tris-HCl, pH 7.5.

After separation of the substances that are active in determining the odor, e.g., by chromatographic methods (HPLC, FPLC) or immunological methods, these substances may be added to cosmetic preparations such as perfumes, emulsions, soaps, oils, gels, creams and the like in appropriate concentrations. Such formulations also form an object of this invention.

One particular feature of the perfume composition according to this invention is that it may consist of two separately formulated products. It is also possible to formulate three separate products.

In the preferred perfume combination according to this invention, the product produced according forms a combination unit with a second product which is also produced by the method, with the provision that the selected allele for the second product is a different allele than the allele for the first product. The allele for the second product also differs by at least one feature from other alleles of the HLA class I molecules. This feature is a so-called rare feature which occurs in less 5%, preferably less than 1% of the world's population (allele frequency).

The combined unit includes two perfume formulations, one of which is provided for or is to be assigned to different partners, preferably different partners of different sexes.

Preferred perfume compositions are characterized in that the alleles HLA-A*6601 and HLA-B*7301; the alleles HLA-B*1301 and HLA-B*2709; the allele HLA-B*2705 with the replacement of the B pocket by the pocket of the HLA-A*0201 allele and HLA-B*7301 are used as starting materials for the separate perfume compositions. These allele pairs form starting materials for corresponding perfume composition pairs, e.g., A and B, perfume A being assigned to partner A and perfume B being assigned to partner B to increase the attractiveness of partners A and B for one another.

BRIEF DESCRIPTION OF THE DRAWINGS

This invention is illustrated in greater detail below by examples. In the respective drawings.

DETAILED DESCRIPTION OF THE INVENTION

EXAMPLE 1

Producing Perfume Component A

Induction

Figure 1:
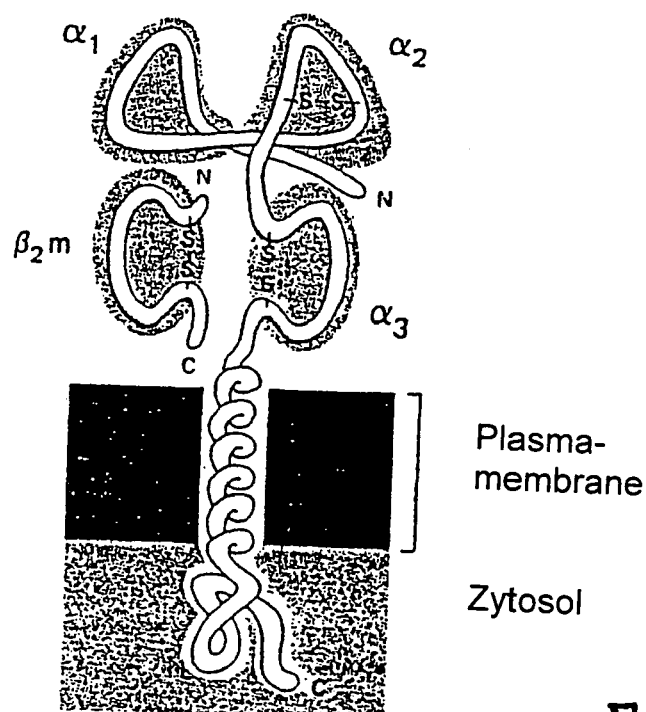
FIG. 1 shows a schematic diagram of an HLA class I molecule with extracellular domains $\alpha_1$, $\alpha_2$, $\alpha_3$; the membrane-anchored heavy chain is not covalently associated with $\beta_2$m.
Figure 2:
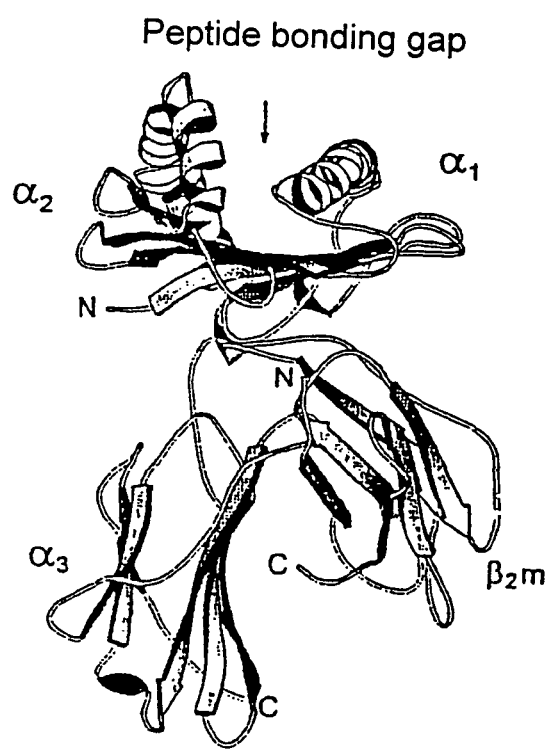
FIG. 2 shows a structure of the extracellular fraction of an HLA class I molecule.
Figure 3:
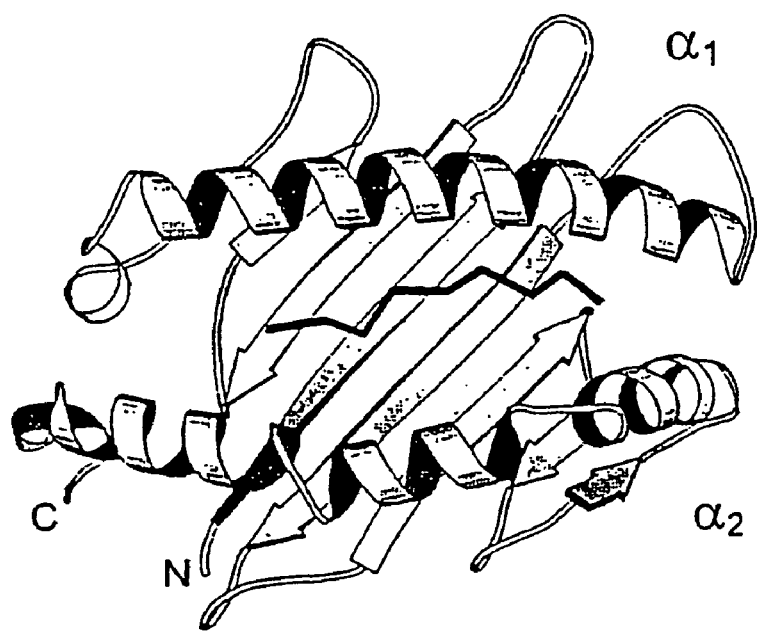
FIG. 3 shows a view from above onto the peptide binding pocket having the peptide bound in a zigzag pattern (HLA-B*3501 with peptide LPPLDITPY).

LB medium=10 g bactotryptone, 5 g yeast extract, 10 g NaCl dissolved in 1 L ddH$_2$O.

300 ml LB/amp medium was inoculated with 3 ml overnight culture (at room temperature) in a 1 L flask and agitated at 300 rpm at 37° C. until reaching an OD$_{560}$ of 0.7. After adjusting the IPTG (IPTG=isopropyl-β-D-thiogalactopyranoside) concentration to 0.4 mM, the bacteria continued to grow for 4 more hours at 37° C. before being centrifuged for 20 minutes at 2700 g. The pellet was used for preparation of inclusion bodies.

For identification of protein-expressing clones after transformation, induction was performed on a smaller scale. Portions of 200 µl LB/Amp were inoculated with a colony in a 96-hole cell culture plate (Costar) and incubated overnight at room temperature. Then 100 µl was removed and placed in a new well together with 100 µl LB/Amp/2×IPTG and left to stand for four hours at 37° C. Then the culture was centrifuged in an Eppendorf vessel, the bacteria placed in a 100 µl SDS specimen buffer (SDS=sodium lauryl sulfate), lysed for 10 minutes at 95° C. and one aliquot was applied to an SDS polyacrylamide gel. Protein-expressing clones had an additional band.

Preparation of Inclusion Bodies

Foreign proteins are often deposited as a denatured precipitant in bacterial cytoplasm. These inclusion bodies can be purified by several centrifugation steps after cell digestion, dissolved in urea and then reconstituted to yield functional proteins.

The pellet obtained after bacterial induction was dissolved in 10 ml lysis buffer (25% sucrose, 1 mM EDTA, 50 mM Tris-HCl, pH 8.0) and 1 mM phenylmethanesulfonic acid fluoride and frozen overnight at −20° C. or processed further immediately. After adding 0.5 ml lysozyme (10 mg/ml lysis buffer) and incubating for 30 minutes on ice, the solution assumed a viscous consistency because of the release of DNA. Adding MgCl$_2$ (to 10 mM), MnCl$_2$ (to 1 mM) and DNase I (to 10 µg/ml) caused the lysate to be reliquified. After centrifuging for 10 minutes at 10,000 g, the pellet was resuspended by ultrasound in 10 ml detergent buffer (0.2M NaCl, 1% deoxycholic acid (Sigma), 1% Nonidet P-40 (Sigma), 2 mM EDTA, 2 mM DTT (dithiothreitol), 20 mM Tris-HCl, pH 7.5) and centrifuged again on ice after incubating for ten minutes. The inclusion bodies were washed four times in Triton buffer (100 mM NaCl, 1 mM EDTA, 2 mM DTT, 0.5% Triton X100 (Serva), 50 mM Tris-HCl, pH 8.0) and dissolved in 4 ml 20 mM Tris-HCl, pH 7.5, 150 mM NaCl, 10 mM DTT.

Reconstitution of the Functional HLA-peptide Complex

The functional molecule HLA A*6601 was reconstituted from the heavy chain $\alpha_1$, $\alpha_2$, $\alpha_3$ domains), dissolved in urea, β$_2$-microglobulin and the peptide X

T

V

XXXXXX

R

K according to the dilution protocol of Garboczi et al. (*Proc. Natl. Acad. Sci. USA*, Vol. 89, 3429–3433, 1992).

The subunits purified in the form of inclusion bodies were dissolved in freshly prepared and filtered urea buffer (50% urea, 50 mM NaCl, 20 mM Tris-HCl, pH 7.5) (30 minutes at room temperature in an agitator), then centrifuged (20 minutes, 10,000 g) and their concentration was determined. The two chains were combined, topped off with urea buffer to 5 ml and diluted in 200 ml reconstitution buffer (400 mM l-arginine, HCl (Sigma), 2 mM EDTA, 5 mM reduced glutathione, 0.5 mM oxidized glutathione, 100 mM Tris-HCl, pH 7.5) containing the peptide. The final concentration of the HLA chain was 1 µM and that of the β$_2$-microglobulin was 2 µM and that of the peptide was 10 µM. The batch remained at 4° C. for 36 hours and was separated on a gel filtration column after concentrating to 1 ml with the help of Centriprep-10 concentration tubes (Amicon).

Gel Filtration

The HLA-peptide complex was purified by means of a Superdex 75-HR column (Pharmacia) equilibrated with 20 mM Tris-HCl, pH 7.5, 150 mM NaCl on which the concentrated restitution batch was separated at a flow rate of 1 ml/min.

Fragmentation 1 mg of the purified HLA-peptide complex in 1 ml buffer (20 mM Tris-HCl, pH 7.5, 150 mM NaCl) is either mixed directly with bacterial pronase type XIV from *Streptomyces griseus* (final concentration 0.1 mg/ml) or added to serum from $\beta_2$m(−/−) mice that could no longer produce $\beta_2$m protein because of defective genes for $\beta_2$m (final concentration of the HLA-peptide complex 1 mg/ml). Before adding the enzyme, induction of the HLA-peptide complexes may be performed in the serum at 4° C. to 40° C. for up to 24 hours; then it is mixed with bacterial pronase type XIV from *Streptomyces griseus* (final concentration 2 mg/ml). Degradation of the proteins is performed at room temperature for 2 hours. Other concentrations of the HLA-peptide complex and the enzyme as well as the degradation time and temperature are possible. The fragmented proteins are either frozen at −80° C. or processed further directly.

Separation

The components that are inactive with respect to scent may be separated by means of Sephadex G-100 in a batch process where the specimen containing the degraded proteins is mixed with Sephadex (1/10 of the volume), incubated for 10 minutes at room temperature briefly. The supernatant contains the components of the specimen that have an active odor effect.

This yields perfume component A.

EXAMPLE 2

Producing Perfume Component B

The procedure followed was the same as that described in Example 1 but the allele used was HLA-B*7301 and as the peptide XRXXXXXXP. The following sets corresponded to those in Example 1, yielding perfume component B after fragmentation and separation

EXAMPLE 3

Perfume Composition (eau de Perfume)

Composition A

At room temperature the following ingredients were mixed together (% by weight);

| | |
|---|---|
| Perfume component A | 11% |
| Ethanol | q.s. to 100 |
| Water | 1% |
| Color blue | 0.05% |

At the same time the following ingredients were mixed together:

Composition B

| | |
|---|---|
| Perfume component B | 10% |
| Ethanol | q.s. to 100 |
| Water | 1% |
| Color yellow | 0.06% |

The two compositions were stored for 10 days at 5° C. to 10° C. thereafter and then packaged as a retail unit. Composition A was next made available to a partner of a committed relationship, and composition B was made available to the other partner of the relationship. Next, the two partners each evaluated the perfume of the other partner as very erotic and attractive.

EXAMPLE 4

Face and Body Cream

Part A

| Phase A (in % by weight) | |
|---|---|
| Propylene glycol dicaprylate | 4 |
| Cetearyl isononanoate | 2.5 |
| Shea butter | 1.0 |
| Dimethicone | 1.2 |
| Phase B | |
| Water | q.s. to 100 |
| Glycerol | 3 |
| Phase C | |
| Preservative | 0.5 |
| Perfume component A | 1.5 |
| Orange dye | 0.08 |

Phase A was heated to 70° C. and phase B was also heated separately to 70° C. Then the two phases were mixed together and the mixture was cooled to 40° C. Next phase C was added and the entire mixture was homogenized.

Part B

The phase composition of phases A and B as in part A of Example 4 was used.

| Phase C | |
|---|---|
| Preservative | 0.5 |
| Perfume component B | 1.5 |
| Blue dye | 0.08 |

These ingredients were processed like those for part A of Example 4. Parts A and B of the cream of Example 4 were finished together as one retail unit. Then part A was made available to a partner of a committed relationship and part B was made available to the other partner of the relationship. Each partner evaluated the perfume of the partner as very attractive.

The invention claimed is:

1. A perfume composition of HLA molecules prepared according to a method whereby
   a) an allele is selected from known HLA alleles of class I such that it differs by at least one feature from other alleles of the HLA class I molecules which occurs in less than 5% of the world's population; or
   b) HLA alleles of class I are selected which have been produced by mutation of existing HLA alleles of class I and do not occur naturally and thus have an incidence of 0%; and
   c) the protein for which the selected allele codes is subjected to assembly in the presence of $\beta_2$-microglobulin ($\beta_2$m) by using a plurality of different peptides having a length of typically 7 to 12 amino acids and with N- and C-termini to form soluble HLA class I molecules consisting of the extracellular domains $\alpha_1$, $\alpha_2$ and $\alpha_3$, $\beta_2$m and a peptide is formed, whereby the peptide is present in bound form in a peptide binding chain of the HLA molecule formed by the extracellular domains $\alpha_1$ and $\alpha_2$; and d) the HLA class I molecules thus formed together with the bound peptides are separated from the other constituents in one purification step; and e) the purified HLA class I molecules are subjected to fragmentation with one or more proteases; and f) the substances that are active in producing the odor and are formed in fragmentation are added either as an individual component or as a mixture to a cosmetic preparation, optionally after first separating the other substances.

2. The perfume composition according to claim 1, wherein the proteases are selected from proteases such as serine proteases, cysteine proteases, aspartate proteases and metal proteases, amino peptidases, dipeptidases, dipeptidyl carboxypeptidases, carboxypeptidases, omega-peptidases.

3. The perfume composition according to claim 1, wherein the protease is pronase.

4. The perfume composition according to claim 1, wherein the alleles HLA-A*6601 and HLA-B*7301, the alleles HLA-B*1301 and HLA-B*2709, the alleles HLA-B*2705 with the replacement of the "B" pocket by the "B" pocket of the HLA-A *0201 allele and HLA-B*7301, are used as starting materials for separate perfume composition pairs.

5. The perfume composition according to claim 1, wherein the HLA class I molecule formed according to point c) or d) is added to a serum from $\beta_2$m (–/–) mice for a period of 1 to 36 hours at 4° C. to 40° C. before subsequent fragmentation.

6. The perfume composition according to claim 1, wherein t the product produced forms a combination unit with a second product which is produced with the provision that the selected allele for the second product is a different allele from the allele for the first product, the allele for the second product also differs by at least one feature by other alleles of the HLA class I molecules, and it occurs in less than 5% of the world's population.

7. The perfume composition according to claim 6, wherein it is in the form of at least one of a clear solution, soap, cosmetic gel, cosmetic emulsion, and a cream, in a concentration of 0.0001 to 20 wt %, based on the total composition.

8. A method for, said method comprising administering topically to each of the partners a different perfume composition of HLA molecules selected from a perfume composition pair, each perfume composition prepared according to a method whereby a) an allele is selected from known HLA alleles of class I such that it differs by at least one feature from other alleles of the HLA class I molecules which occurs in less than 5% of the world's population; or b) HLA alleles of class I are selected which have been produced by mutation of existing HLA alleles of class I and do not occur naturally and thus have an incidence of 0 %; and c) the protein for which the selected allele codes is subjected to assembly in the presence of $\beta_2$-microglobulin ($\beta_2$m) by using a plurality of different peptides having a length of typically 7 to 12 amino acids and with N- and C-termini to form soluble HLA class I molecules consisting of the extracellular domains $\alpha_1$, $\alpha_2$ and $\alpha_3$, $\beta_2$m and a peptide is formed, whereby the peptide is present in bound form in a peptide binding chain of the HLA molecule formed by the extracellular domains $\alpha_1$ and $\alpha_2$; and d) the HLA class I molecules thus formed together with the bound peptides are separated from the other constituents in one purification step; and e) the purified HLA class I molecules are subjected to fragmentation with one or more proteases; and f) the substances that are active in producing the odor and are formed in fragmentation are added either as an individual component or as a mixture to a perfume preparation, optionally after first separating the other substances.

9. The method as in claim 7, wherein the first partner is assigned the allele HLA-A*6601 and the second partner HLA-B*7301; the first partner is assigned the allele HLA-B *1301 and the second partner HLA-B*2709; or the he first partner is assigned allele HLA-B*2705 with the replacement of the "B" pocket by the "B" pocket of the HLA-A*0201 allele and the second partner HLA-B*7301.

* * * * *